United States Patent [19]
Plotnikov et al.

[11] Patent Number: 5,967,659
[45] Date of Patent: Oct. 19, 1999

[54] ULTRASENSITIVE DIFFERENTIAL MICROCALORIMETER WITH USER-SELECTED GAIN SETTING

[75] Inventors: Valerian V. Plotnikov, Sunderland; John F. Brandts, Leeds; J. Michael Brandts, Holyoke, all of Mass.

[73] Assignee: MicroCal, Incorporated, Northampton, Mass.

[21] Appl. No.: 09/154,055

[22] Filed: Sep. 16, 1998

Related U.S. Application Data

[62] Division of application No. 08/729,433, Oct. 11, 1996, Pat. No. 5,813,763.

[51] Int. Cl.[6] .................................................. G01N 25/20
[52] U.S. Cl. .............................. 374/11; 374/31; 422/51; 436/147; 702/130
[58] Field of Search .................................. 374/11, 10, 31, 374/34; 422/51, 109; 436/147; 702/130

[56] References Cited

U.S. PATENT DOCUMENTS

| | | | |
|---|---|---|---|
| 3,022,664 | 2/1962 | Stolwijk | 374/31 |
| 3,319,456 | 5/1967 | Speros et al. | 374/11 |
| 3,858,433 | 1/1975 | Nearhoof | 374/10 |
| 4,255,961 | 3/1981 | Biltonen | 374/11 |
| 4,333,332 | 6/1982 | Privalov | 374/10 |
| 4,530,608 | 7/1985 | O'Neill | 374/11 |
| 4,812,051 | 3/1989 | Paulik et al. | 374/10 |
| 4,892,707 | 1/1990 | Stockton et al. | 422/51 |
| 5,248,199 | 9/1993 | Reading | 374/11 |
| 5,439,291 | 8/1995 | Reading | 374/11 |
| 5,547,282 | 8/1996 | Pinhack et al. | 374/36 |
| 5,599,104 | 2/1997 | Nakamura et al. | 374/12 |

FOREIGN PATENT DOCUMENTS

| | | | |
|---|---|---|---|
| 0261949 | 5/1968 | Austria | 374/10 |
| 2370965 | 7/1978 | France | 374/11 |
| 0027496 | 3/1978 | Japan | 374/11 |
| 0732689 | 5/1980 | U.S.S.R. | 374/11 |

OTHER PUBLICATIONS

Filatous, G. et al., "An Amplifier Controlled Adiabatic Calorimeter", Dev. Sci. Instrum., vol. 42, No. 4, pp. 447–450 (Apr. 1971).

Chowdry et al., "Differential Scanning Calorimetry: Applications in Biotechnology", Trends in Biotechnology, 7:11–18 (1989), No Month.

Brandts et al., "An Instrument for Rapid Determination of Binding Constants for Biomolecules", American Laboratory, 30 (May 1990).

Ladbury, "Counting the Calories to Stay in the Groove", Structure, 3:635–639 (Jul. 15, 1995).

Cooper et al., "Introduction to Microcalorimetry and Biomolecular Energetics", Methods in Molecular Biology, vol. 22, Chapters 9–11, 109–150 (1994), No Month.

Clarebrough et al., "The determination of the energy stored in a metal during plastic deformation," in Proceedings of the Royal Society of London. A215:pp. 507–524, Nov.–Dec. 1952.

*Primary Examiner*—Diego Gutierrez
*Assistant Examiner*—Stanley J. Pruchnic, Jr.
*Attorney, Agent, or Firm*—Fish & Richardson P.C.

[57] ABSTRACT

A differential calorimeter includes sample and reference cells, a thermal shield surrounding these cells, heating devices thermally coupled to the thermal shield and the cells, a temperature monitoring system for monitoring temperature of the shield, cell temperatures and temperature differentials between the cells and the shield, and a control system. The control system has input lines to receive signals from the temperature sensors and output lines connected to the heating devices. The control system is configured to generate output signals for control of heating devices. A gain setting and scan rate are selected by means of a user interface. The output control signals are functions of input temperature signals and the user-selected gain setting, and also functions of input temperature signals and the user-selected scan rate using a mapping function stored in memory.

6 Claims, 4 Drawing Sheets

ULTRASENSITIVE DIFFERENTIAL MICROCALORIMETER WITH USER-SELECTED GAIN SETTING

This application is a divisional of application Ser. No. 08/729,433, filed Oct. 11, 1996, now U.S. Pat. No. 5,813,763.

BACKGROUND OF THE INVENTION

This invention relates generally to microcalorimeters and more specifically to features that improve the performance of ultrasensitive microcalorimeters.

Ultrasensitive microcalorimeters are broadly utilized in fields of biochemistry, pharmacology, cell biology, and others. Calorimetry provides a direct method for measuring changes in thermodynamic properties of biological macromolecules. Ultrasensitive microcalorimeters are typically twin cell instruments in which properties of a dilute solution of test substance in an aqueous buffer in a sample cell is continuously compared to an equal quantity of aqueous buffer in a reference cell. Measured differences between the properties of two cells, such as temperature or heat capacity, can be attributed to the presence of the test substance in the sample cell.

There are two popular types of microcalorimeters, namely, a differential scanning microcalorimeter and an isothermal titration calorimeter. The differential scanning calorimeter automatically raises or lowers the temperature at a given rate while monitoring the temperature differential between cells. From the temperature differential information, small differences in the heat capacities between the sample cell and the reference cell can be determined and attributed to the test substance. One of the popular uses of scanning calorimetry is to measure the thermodynamic properties for thermally-induced structural transitions of biopolymers in very dilute solutions, where approximately 0.1% of the mass of solution is the biopolymer itself and more than 99.9% is the solvent. Even using the differential method, scanning calorimeters must have extremely high sensitivity in order to measure properties of the biopolymer in the presence of an overwhelming amount of the aqueous solution.

The isothermal titration calorimeter (ITC) is also a twin-cell differential device, but operates at a fixed temperature while the liquid in the sample cell is continuously stirred. The most popular application for titration calorimetry is in the characterization of the thermodynamics of molecular interactions. In this application, a dilute solution of the test substance (e.g., a protein) is placed in the sample cell and, at various times, small volumes of a second dilute solution containing a ligand which binds to the test substance are injected into the sample Cell. The instrument measures the heat which is evolved or absorbed as a result of the binding of the newly-introduced ligand to the test substance. From results of multiple-injection experiments, the binding constant, heat of binding, and stoichiometry of binding can be determined.

The sensitivity of either type of microcalorimeter is limited by heat exchange between the cells and its surroundings. When there is no heat exchange between the cells and the surroundings, the microcalorimeter is adiabatic. In order to limit uncontrolled heat exchange between the cells and the ambient environment, the cells are surrounded by a thermal shield containing controlled heating and cooling means. The thermal shield has a thermocouple-activated sensor which measures differential temperature between the shield and the cells. When this temperature differential is minimized, heat exchange between the cells and shield is also minimized.

Scanning differential microcalorimeters generally operate in one of two modes: adiabatic and non-adiabatic. In the adiabatic mode, the temperature of the cells is driven at a constant rate and the temperature of the thermal shield is maintained equal to the temperature of the cells by a differential control system. Measurement of the temperature differential between the shield and cells goes to an input of a high-sensitivity amplifier and then to a controller. The controller heats and/or cools the shield to balance the temperature between the shield and the cells. The benefit of the adiabatic mode is high sensitivity resulting from minimal heat exchange between cells and shield. However, since the cells cannot be directly cooled, those calorimeters which upscan (heat cells) in the adiabatic mode must downscan (cool cells) using the non-adiabatic mode. Also, when desiring to operate in an adiabatic mode at constant temperature, constancy in temperature is difficult to maintain for long periods of time.

In the non-adiabatic mode, the temperature change of the shield follows a prespecified path and the temperature of the cells follow that of the shield through heat conduction. Typically, the actual temperature of the shield is repeatedly measured and compared to the desired temperature. Differences between these two temperatures are used to actively modify the heating and cooling of the shield. Since heat conduction between cells and shield is slow, the temperature of the cells can lag the temperature of the thermal shield by 5° C. or more at scanning rates of 60–120° C./hr. A benefit of this type of calorimeter is that heating or cooling of the cells is possible using the same mode of operation. Another advantage is that when operating at constant temperature, there is very little temperature drift even over long periods of time. However, the non-adiabatic mode has several drawbacks, the most important being that it is less sensitive than the adiabatic mode of operation. First, its sensitivity is limited by the inability to uniformly control the temperature of the shield, and second, the baseline is difficult to reproduce from scan to scan due to the very high heat leak from the cells to the shield.

Microcalorimeters typically compensate for differential heat effects between the two cells by one of two methods: passive compensation or active compensation. In microcalorimeters using passive compensation, temperature differences arising from heat events dissipate due to differential heat flow between the two cells. In microcalorimeters using active compensation, temperature differentials between the two cells activate a power feedback system which supplies appropriate heat directly to the cooler cell. Actively heating the cooler cell occurs in addition to differential heat flow, thereby more quickly reducing temperature differences between cells. The primary advantage of active compensation is the much shorter time required to equilibrate the two cells, resulting in a fast instrument response time. The primary disadvantage is that the feedback system generates noise and-baseline irregularity over and above that exhibited with passive compensation.

SUMMARY OF THE INVENTION

In general, in one aspect, the invention is a calorimeter which includes sample and reference cells, a thermal shield surrounding these cells, a heating device thermally coupled to the thermal shield, temperature sensors for monitoring a temperature of the shield and a temperature differential between the shield and the cells, and a control system. The control system has an output line connected to the heating device and input lines to receive signals from the temperature sensors. The control system is configured to generate on its output line an output signal which is a function of both the input signals received on its input lines.

In preferred embodiments, the control system includes a memory which stores a mapping function. The mapping function maps the temperature of the thermal shield, which is monitored by the first temperature sensor, to a correction term. The control system combines this correction term with the second signal from the temperature differential sensor to generate the output signal to the heating device for the thermal shield.

In general, in another aspect, the invention is a calorimeter which includes sample and reference cells, a thermal shield surrounding the cells, a heating device thermally coupled to both of the cells, a temperature monitoring system which monitors the temperature of at least one of the cells, and a control system which during operation causes the heating device to heat both the sample and reference cells at a user-selected scan rate. The control system has an output line connected to the heating device and an input line which receives a signal from the temperature monitoring system. The control system is configured to generate on its output line an output signal which is a function of both a user-selected scan rate and the signal on the input line.

In preferred embodiments, the control system includes a memory storing a mapping function which maps both the monitored temperature and the user-selected scan rate to a control parameter. The control system generates an output signal on the output line that is derived from the control parameter and is sent to the heating device.

In general, in still another aspect, the invention is a method of generating a mapping function for producing improved adiabatic performance of a calorimeter. The method includes the steps of (a) choosing a plurality of temperatures within a range of temperatures; (b) heating the sample cell in the calorimeter to a selected one of the plurality of temperatures; (c) heating the thermal shield so as to minimize a temperature differential between the sample cell and the thermal shield; (d) when a temperature of the calorimeter reaches the selected temperature, discontinuing the heating of the sample cell; (e) recording a drift in the temperature of the calorimeter over a period of time; (f) determining a correction term for the selected temperature which minimizes the drift in the temperature; (g) repeating steps (b–f) for the rest of the plurality of temperatures; and (h) deriving the mapping function from the correction terms for the plurality of temperatures.

In preferred embodiments the method further includes fitting a polynomial to the correction terms for the plurality of temperatures, wherein the polynomial is the mapping function.

In general, in a further aspect, the invention is a method of generating a mapping function for producing a more constant scan rate in a calorimeter. The method includes the steps of: (a) selecting a scan rate within a range of scan rates; (b) heating the sample cell so that its temperature changes at a rate that is determined by the selected scan rate; (c) recording the temperature of the sample cell as a function of time to determine a measured scan rate for the sample cell; (d) from the recorded temperature, determining an actual scan rate at a plurality of temperatures; and (e) based upon an amount by which the actual scan rate differs from the selected scan rate, determining for the selected scan rate a correction term at each of the plurality of temperatures which when applied to the step of heating the sample cell produces an actual scan rate for the cell that is more constant over temperature than the measured scan rate, wherein the mapping function is derived from the correction terms.

In preferred embodiments the method may include one or more of the following features. The method may further includes the steps of: (f) performing steps (b–e) for a plurality of different selected scan rates within the range of scan rates. In addition, the method may further include generating the mapping function from the correction terms for the plurality of scan rates and the plurality of temperatures at each scan rate. The method may also include the step of (f) fitting a polynomial to the correction terms that were obtained at the plurality of temperatures for the selected scan rate. The method may also include the step (f) for performing steps (b–e) for a plurality of different selected scan rates within the range of scan rates to arrive at a plurality of polynomials, one for each of said plurality of scan rates. In addition, the method may further include the step in which for a corresponding term of each of the plurality of polynomials, fitting a second polynomial to coefficients of those corresponding terms so that the second polynomial expresses the coefficient as a function of scan rate.

In general, in still a further aspect, the invention is a differential calorimeter including sample and reference cells, a first heating device thermally coupled to the sample cell, a second heating device thermally coupled to the reference cell, a temperature sensor which monitors a temperature differential between sample and reference cells, and a control system. The control system has an output line connected to at least one of said heating devices, an input line connected to the temperature sensor, and a user-interface. The user-interface permitting a user-selected gain setting, wherein the control system is configured to provide on its output line an output signal which is given by the product of the user-selected gain setting and the temperature differential from the input line.

Other advantages and features of the invention will become apparent from the following description of the preferred embodiment and from the claims.

DESCRIPTION OF THE INVENTION

Figure 1:
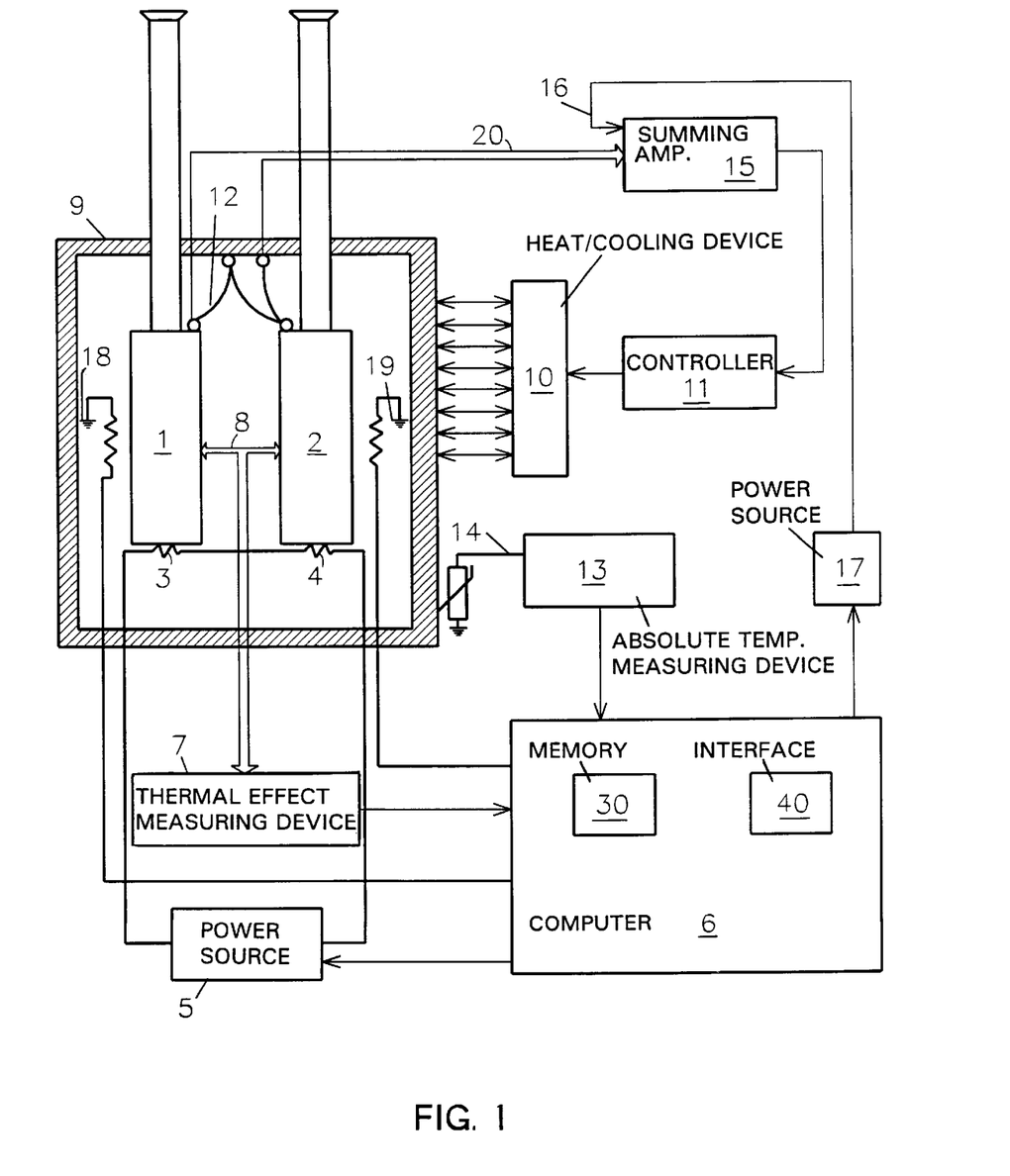
FIG. 1 shows a schematic of the differential microcalorimeter instrument.

A schematic diagram of an embodiment of the improved differential microcalorimeter is shown in FIG. 1. There are two cells, a reference cell 1 and a sample cell 2, each identical in volume and mass, and assembled with inlet capillary tubes and matched heating elements 3 and 4. These cells are of the total-fill type, with the test liquid occupying the entire volume of each cell and capillary tube. The heating elements 3 and 4 are driven by a power source 5 which is controlled by a computer 6. The computer includes a interface 40, so that the user may input specifications, and a memory 30 for storage, for example, a hard drive or random access memory. The heating elements 3 and 4 are matched and driven simultaneously by power source 5, so cells 1 and 2 are heated at an identical rate, which is controlled by the computer. The rate at which the temperature of the cells changes is referred to as the scan rate and is specified by the user through the computer-interface 40. A thermal effect measuring device 7 is connected to a sensor 8 that measures the difference in temperature between the two cells. Typical sensors include wire thermocouples or semiconducting thermocouples. The temperature differential is measured periodically as the cells are being heated during a scan. The temperature differential data is then sent from thermal effect measuring device 7 to computer 6, where it is saved along with the time of the measurement in the computer memory 30.

The cells 1 and 2 are surrounded by a thermal shield 9. During adiabatic operation, the shield helps minimize heat exchange between the cells and their surroundings. The temperature of thermal shield 9 is monitored by an absolute temperature measuring device 13 which is activated by a sensor 14 (typically a platinum resistance thermometer device or RTD) which is mounted on the thermal shield. Thermal shield 9 is connected to a heating and cooling device 10 (typically an array of Peltier devices) which is operated by a controller 11. The signal to the controller 11 comes from the output of a summing amplifier 15 which receives two inputs. The first input 20 receives its signal from sensor 12 that monitors the difference between the temperature of thermal shield 9 and the average temperature of the two cells 1 and 2. The second input 16 receives its signal from a power source 17 whose output is controlled by computer 6. The output from absolute temperature measuring device 13 is sent to computer 6 and used to determine the appropriate signal to send to power source 17 and subsequently onto the summing amplifier 15. The absolute temperature information is repeatedly stored in the computer memory 30 in conjunction with the temperature differential between cells and the time of the measurement. The operating range for the calorimeter in terms of the temperature at which the cells and shield can be operated is −20° C. to 150° C.

Additional cell heaters 18 and 19 are located on reference and sample cells 1 and 2, respectively. The power to each of these heaters is independently controlled directly by the output of computer 6. These cell heaters 18 and 19, which generate only small amounts of heat, are used to actively reduce any temperature differential between cells. Through the computer interface 40, the user can select between passive compensation, in which additional heaters 18 and 19 are not used, or various levels (typically low, medium, and high) of active compensation, in which these additional heaters are used by computer 6 to actively minimize the temperature differential between cells 1 and 2. The choice of passive compensation or various levels of active compensation is equivalent to a selection between a number of instrument response times.

Improvement of Adiabatic Operation

The calorimeter can operate in one of three modes: adiabatic, improved adiabatic, and non-adiabatic. Selection of a particular mode of operation is made through computer interface 40. In the adiabatic mode, the second input 16 to the summing amplifier 15 is deactivated. As described previously, the first input 20 of the summing amplifier receives a signal from sensor 12 which monitors the difference between the temperature of thermal shield 9 and the average temperature of the two cells 1 and 2. Based only on the temperature differential signal received at the first input 20, the summing amplifier 15 sends a signal to controller 11. In turn, controller 11 regulates heating and cooling device 10 for thermal shield 9 in relation to the signal from summing amplifier 15, thereby minimizing the temperature difference between shield 9 and the cells 1 and 2. In this way, the temperature of thermal shield 9 follows the temperature of the cells 1 and 2, which is controlled by computer 6 via power source 5 and cell heaters 3 and 4.

However, the adiabatic mode of operation does not provide completely adiabatic performance. For example, if cells 1 and 2 are raised to a temperature above room temperature and then cell heaters 3 and 4 are turned off, but the calorimeter remains in the adiabatic mode, the differential temperature between the shield and the cells will continue to be actively minimized as described above. It is observed empirically, however, that the absolute temperature of the cells and shield will drift downward. The rate of this temperature drift can approach 1–2° C./hour when the temperature of the calorimeter is about 70° C. If the calorimeter performed adiabatically, no drift in temperature would be observed.

To improve adiabatic performance, the calorimeter can operate in the improved adiabatic mode. In this mode of operation, both inputs to summing amplifier 15 are activated. In addition to the signal received at the first input 20 from the differential temperature sensor 12, summing amplifier 15 receives a second signal at the second input 16 from computer 6 via power source 17. This second signal represents a correction factor generated by an empirically-derived equation which is stored in computer memory 30. The correction factor is a function of the current temperature of thermal shield 9 which is repeatedly measured and stored in computer memory 30 during operation. The two signals received by summing amplifier 15, i.e. the signal from the differential temperature sensor 12 and the correction factor, are added together and sent to controller 11 which regulates the heating and cooling device 10 accordingly. More generally, any summing circuit may be used which functionally combines the two input signals, whether by simple addition or by some other operation.

The correction factor is repeatedly recomputed and revised as the cells are being heated during a scan or as they are being maintained at a particular temperature. The correction factor attempts to compensate for factors that limit adiabatic performance, such as heat exchange between the shield and the surroundings and temperature gradients within the calorimeter.

The calorimeter can also operate in a non-adiabatic mode. In this case, the cell heaters 3 and 4 are deactivated. The signal from computer 6 to the second input 16 of summing amplifier 15, via second power source 17, gives a specified rate of heating and cooling thermal shield as determined by a file specified by the user through computer interface 40 and stored in computer memory 30. The file is a function of the temperature of thermal shield 9 which is measured repeatedly during the scan. A signal is sent from summing amplifier 15 to controller 11 which in turn regulates heating and cooling device 10 accordingly. In this case, the temperature of the cells 1 and 2 follow the temperature of thermal shield 9 by heat conduction. Since the heat conduction process is relatively slow, the temperature of the cells typically lags behind the temperature of the thermal shield, in contrast to the former two cases where the temperature of the thermal shield is actively driven to follow the temperature of the cells.

Determination of Equation for Improved Adiabatic Operation

Figure 2:
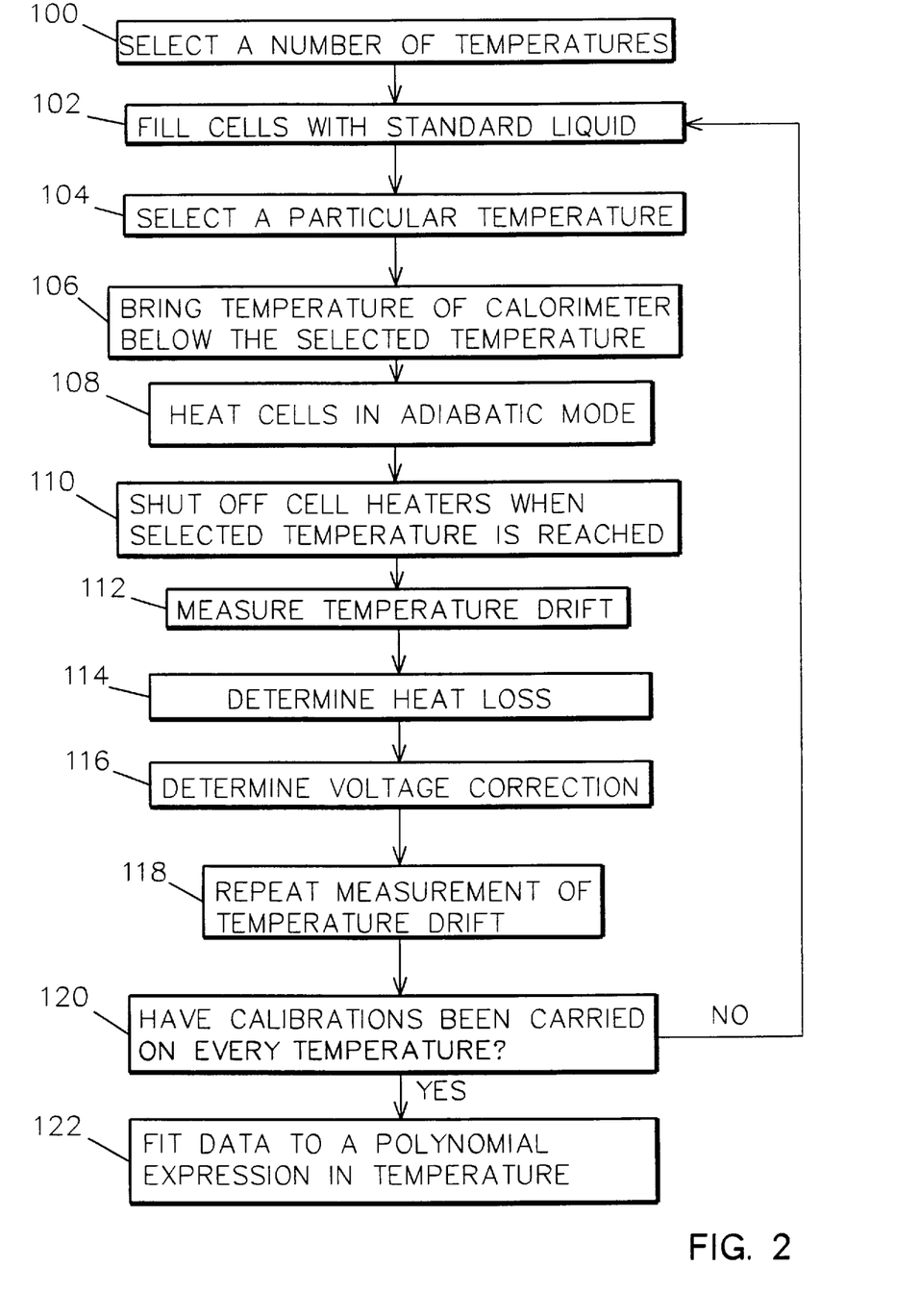
FIG. 2 shows a flow diagram of the method for determining the temperature-dependent equation that provides improved adiabaticity.

The empirically-derived equation which gives the correction factor for improved adiabaticity is determined in a manner shown in FIG. 2. A plurality of temperatures within a range of temperatures are selected. The temperature range should span the scanning range of the instrument, typically, −20° C. to 150° C., and the temperatures within the range should be spaced sufficiently close together, e.g. every 5° C., so the correct signal at intermediate temperatures can be accurately interpolated (step 100). Cells 1 and 2 are filled with a standard liquid, typically water, and allowed to equilibrate thermally for a short time prior to the start of scanning (step 102). The lowest temperature is selected to begin the calibration run (step 104). The entire apparatus is brought to an initial temperature below the selected temperature by heating or cooling thermal shield 9 using the non-adiabatic mode of operation (step 106). Then a temperature upscan is started by supplying a given constant voltage from power supply 5 to cell heaters 3 and 4, which heats the cells at a nearly constant rate. The upscan is initiated using the adiabatic mode of operation so the temperature of the thermal shield is made to follow the average temperature of the cells 1 and 2 (step 108). Once the temperature of thermal shield 9, which is monitored, reaches the selected temperature, the power to cell heaters 3 and 4 is shut off (step 110). The instrument still in the adiabatic mode, the difference between the temperature of thermal shield 9 and the average temperature of the two cells 1 and 2 is actively minimized. The absolute temperature of thermal shield 9 is periodically measured and recorded (step 112).

The temperature of the shield will tend to drift toward room temperature reflecting heat exchange from the cells to the surroundings via the shield. Using the temperature drift data collected in step 112 and knowledge of the heat capacity of thermal shield 9 and cells 1 and 2, the rate of heat exchange between the calorimeter and the surroundings is then determined (step 114). Knowing the rate determined in step 114 and the heating and cooling characteristics of device 10, enables one to then compute a correction which must be sent to controller 11 to compensate for the heat exchange between the calorimeter and the surroundings and eliminate the temperature drift. This corrected voltage is sent to the second input 16 of summing amplifier 15 from computer 6 via power source 17 (step 116).

The temperature of thermal shield 9 is again measured as a function of time. If it does not remain substantially constant, the signal to the second input 16 of summing amplifier 15 is iteratively modified from the initial result until the measured temperature of the shield remains substantially constant. This final signal is recorded and stored in computer memory 30 along with the temperature (step 118).

Steps 100–118 are then repeated for each of the remaining temperatures selected in step 100 (step 120). When calibrations are completed for all temperatures, the resulting data represents a correction factor as a function of temperature. A temperature-dependent polynomial equation is fitted to the recorded data using standard non-linear least-squares regression techniques (step 122).

Improving Constancy of Scan Rate

Figure 3:
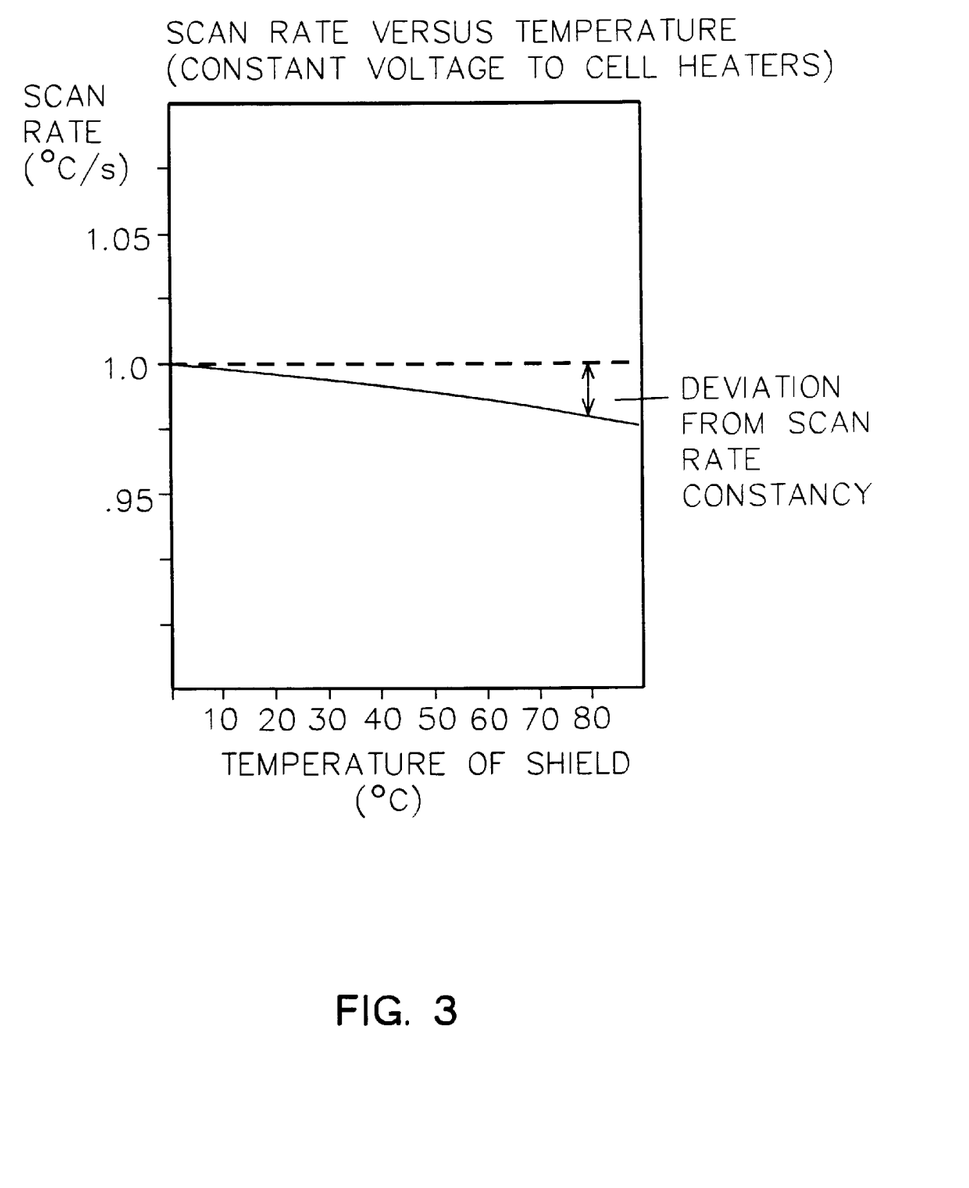
FIG. 3 shows a typical plot of scan rate versus temperature for a constant voltage applied to the cell heaters.

During adiabatic or improved adiabatic modes of operation, the instrument produces improved constancy of scan rate. When power supply 5 provides a constant voltage to cell heaters 3 and 4, the temperature change in the cells 1 and 2 will initially rise linearly with time. This initial scan rate is referred to as the nominal scan rate. As the temperature rises, however, the current scan rate will diverge from the nominal scan rate. These deviations arise due to various factors including for example temperature-dependent resistivity of cell heaters 3 and 4, the temperature-dependent heat capacity of cells 1 and 2 and their contents, and departures from adiabatic operation. FIG. 3 illustrates the typical departure from a constant scan rate for a particular constant voltage. To produce a constant scan rate, computer 6 via the power source 5 sends a variable voltage to cell heaters 3 and 4 as determined by a second empirically-derived equation. This equation depends functionally on the desired scan rate, which is specified by the user prior to the scan through computer interface 40, and the temperature of thermal shield 9. In other words, the voltage signal to cell heaters 3 and 4 is updated repeatedly based on the measured temperature of thermal shield 9.

Equation for Improved Constancy of Scan Rate

Figure 4:
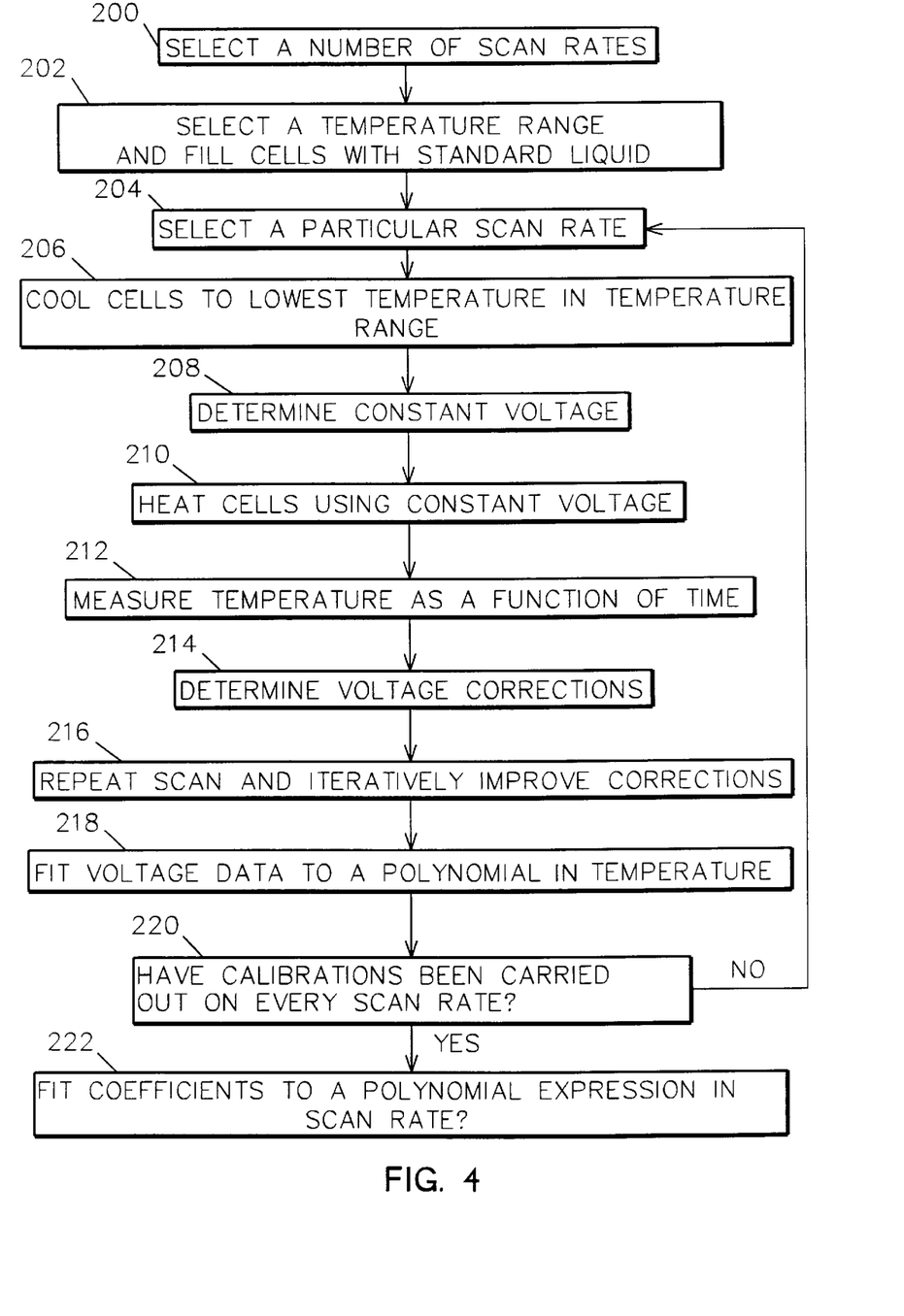
FIG. 4 shows a flow diagram of the method for determining the equation that improves scan-rate constancy.

The second equation which provides improved constancy of scan rate is determined empirically using the method shown in FIG. 4. The user selects a number of desired scan rates which span the range of scan rates that the user intends to employ. The selected scan rates are spaced close enough together that the correct voltage values can be interpolated for intermediate desired scan rates (step 200). The user then selects a temperature range which spans the temperature over which the instrument will be used. To perform the calibration, cells 1 and 2 are first filled with a standard liquid. (step 202). From the scan rates selected in step 200, a particular scan rate is selected (step 204). Using the non-adiabatic mode of operation, thermal shield 9 is cooled such that the temperatures of thermal shield 9 and cells 1 and 2 are at the lowest temperature in the temperature range selected in step 202 (step 206). Using knowledge of the temperature-dependent resistance of cell heaters 3 and 4 and the heat capacity of cells 1 and 2 and their contents, the constant voltage required to produce the selected scan rate at the current temperature is determined (step 208). Then, the constant voltage determined in step 208 is supplied to cell heaters 3 and 4 and the instrument is operated in the improved adiabatic mode (step 210). As the cells are being heated, the temperature of thermal shield 9 is measured as a function of time at intervals of, typically, five to one hundred seconds (step 212). Using the data from step 212, the actual scan rate as a function of temperature is computed.

By measuring the difference between actual scan rate and the nominal scan rate at each temperature, and by knowing the temperature-dependent resistance of cell heaters 3 and 4 and the heat capacity of cells 1 and 2 and their contents, a voltage correction can be computed for each temperature for which data was taken. The corrected voltage, when applied to the heaters, will produce a scan rate which more closely approaches the nominal scan rate (step 214).

To further improve the voltage correction, the scan is repeated using the corrected voltages determined in step 214. The voltage corrections are then iteratively modified until the desired rate of scan constancy is achieved. The final voltage as a function of temperature is recorded and stored to computer memory 30 over the temperature range selected in step 202 (step 216).

A temperature-dependent polynomial equation is fit to the voltage V versus temperature T data from step 216 using standard non-linear least-squares regression techniques. The equation is parametrized by the particular scan rate $r_i$ selected in step 204. The equation is shown in (1):

$$V(r_{1,T)} = a_i + b_i T + c_i T^2 + d_i T^3 + \ldots \qquad (1).$$

The fit provides values for coefficients $a_i$, $b_i$, $c_i$, $d_i$, . . . , which give the dependence of the function $V(r_i,T)$ on a particular order of temperature T for the selected scan rate $r_i$ (step 218).

Steps 204–218 are repeated for each scan rate selected in step 200 (step 220). Once calibrations are completed for all scan rates, coefficients determined in step 218 are grouped together according to the order of temperature to which they apply. From this data, the set of coefficients for a particular order of temperature can be fit to a polynomial equation in scan rate r using standard non-linear least-squares methods:

$$a = C_{1a} + C_{2a}r + C_{3a}r^2 + \cdots \quad (2a)$$

$$b = C_{1b} + C_{2b}r + C_{3b}r^2 + \cdots \quad (2b)$$

...

After this exercise is completed, the set of equations (2a), (2b), . . . , can be substituted into equation (3) below:

$$V(r,T) = a(r) + b(r)T + c(r)T^2 + d(r)T^3 + \ldots \quad (3)$$

yielding a single equation that gives voltage as a function of temperature and desired scan rate (step 222).

The equation derived by the above method depends on the heat capacity of the test solution in the cells. Water is the most appropriate test solution for calibration, since most experiments are carried out using aqueous solutions. Experiments using non-aqueous solvents can be accommodated by repeating the method above with the appropriate test solution.

User-Selectable Response Time

The instrument allows the user to select, through computer interface 40, among a number of instrument response times. The instrument response time characterizes the rate of thermal equilibration between reference cell 1 and sample cell 2. A heat-producing event which occurs in one cell and not the other, will produce a temperature differential between cells. The temperature differential will dissipate over time as a result of thermal conduction between cells, i.e. passive compensation. The additional cell heaters 18 and 19 can be used to increase the rate of thermal equilibration between cells by heating cells differently in order to minimize the temperature differential between them, i.e. active compensation.

The different choices of response time for this instrument are typically in the range of three to thirty-five seconds. Selection of the longest response time corresponds to passive compensation, in which the additional cell heaters 18 and 19 are not used. Shorter response times require active compensation and correspond to a particular gain setting in the computer. The computer multiplies the gain setting by the measured temperature differential between cells to determine the voltages used to differentially heat cell heaters 18 and 19.

During active compensation the instrument operates as follows. Cell heaters 3 and 4, which are controlled by computer 6 via power source 5, initiate a scan by heating cells 1 and 2 at a specified rate. In addition, a small constant voltage is applied to cell heater 18 which is connected to reference cell 1. Because cell heater 18 provides a constant voltage to reference cell 1, sample cell 2 can be heated or cooled relative to reference cell 1 by adjusting the voltage to cell heater 19. When a temperature in the cells is reached that triggers a heat producing event (or possibly a heat absorbing event) in sample cell 2, a temperature differential is measured by sensor 8 and transmitted to computer 6 via thermal effect analyzer 7. The computer multiplies this off-balance signal by the user-selectable gain setting to proportionally adjusts the voltage to cell heater 19 to drive the temperature differential to zero. Measurement of the temperature differential between cells and subsequent adjustment of the voltage to cell heater 19 occur repeatedly throughout the scan. In this way, the temperature differential between cells is actively minimized.

Use of a larger gain setting will produce a shorter response time. However, if the gain setting is too large, the differential heating between cell heaters 18 and 19 will be too large, and the temperature of the sample cell will overshoot the temperature of the reference cell, thereby introducing oscillations in the temperature differential data that is being saved to computer memory 30. The onset of these oscillations provide the upper bound on the maximum gain setting and therefore the lower bound for the shortest selectable instrument response time.

During a scan, time, temperature, and temperature differential between cells are repeatedly being stored to computer memory 30. The temperature differential data at each temperature is usually converted to a power differential that quantifies heat producing events at that temperature from constituents in sample cell 2 that are not present in reference cell 1. This conversion depends on the selection of response time and the correct conversion factors are stored in the computer memory 30 prior to operation.

Determinations of the correct factors to convert a temperature differential between cells to a power differential between cells is well-known in the art and include the following calibration. The cells 1 and 2 are filled with identical liquids, typically water, and allowed to equilibrate. At this time the temperature differential between cells has a null baseline. Thereafter, a known increase (or decrease) in constant power is imparted by reference cell heater 18 to reference cell 1. This will cause the temperature of reference cell 1 to rise relative to the temperature of sample cell 2. The temperature will not rise indefinitely, however, because of increased thermal conduction from reference cell 1 to sample cell 2, i.e. passive compensation. In addition, if active compensation is selected, the sample cell 2 will be heated by cell heater 19 in proportion to the product of the gain setting and the current temperature differential. The temperature differential will increase until the heat produced by cell heater 18 to reference cell 1 is offset by the combination of passive and active compensation which provide heat flow into the sample cell 2. Therefore, the temperature differential starts at a null baseline and rises, over a period of time, to a new non-zero baseline, subsequent to a constant power differential being externally applied to reference cell 1. The period of time over which the temperature differential rises quantifies the response time for a particular gain setting. One measure is the referred to as the response half-time, which is the time it takes for the temperature differential to go from the null baseline to a point half-way in between the null baseline and the final non-zero baseline. The total measured change in temperature differential produced by the known power differential gives the conversion factor between these quantities for a particular selection of response time. During subsequent operation, the measured temperature differential can be converted to the correct power differential using the empirically-determined conversion factor for the appropriate response time setting.

The conversion factors can also be determined using a slightly different calibration method. In this case, the known power differential to the reference cell 1 is maintained only for a short period of time, and in effect a heat pulse of known total energy is imparted to the reference cell. This will produce a transient in the temperature differential data. From the integrated area under the transient, relative to the baseline, the correct conversion factor can be determined for each gain setting.

Other embodiments are also within the scope of the invention. For example, in the above description the temperature of the cells was determined by adding the temperature of the thermal shield to the temperature differential between the cells and the shield, both of which are measured. Alternatively, the temperature of the cells may be measured with a different combination of temperature sensors or the temperature of the calorimeter can be measured at other locations within the system. In addition, the improved adiabatic mode of operation can be applied to an isothermal titration calorimeter, or other types of isothermal calorimeters, or also, to a scanning calorimeter operating in an isothermal mode. In these cases, the temperature of the cells is brought to a selected temperature and thereafter the temperature is made to remain constant by operating in the improved adiabatic mode without any voltage to cell heaters 3 and 4. Furthermore, the empirically-determined transformations for improving adiabatic operation and improving scan rate constancy, need not be represented by equations. Rather, the transformation could be represented, for example, by neural network or table of values from which intermediate values are interpolated.

Other embodiments of the design include cells without filling tubes, cells which are removable from the inside of the shield, or a multilayer thermal shield.

What is claimed is:

1. A differential calorimeter comprising:

a sample cell;

a reference cell;

a first heating device thermally coupled to the sample cell;

a second heating device thermally coupled to the reference cell;

a temperature monitoring system which monitors a temperature differential between the sample and reference cells; and a control system which has an output line connected to at least one of said first and second heating devices, an input line connected to said temperature monitoring system, and a user-interface through which a user selects a user-selected gain setting, wherein the control system is configured to provide on its output line an output signal which is a function of both the user-selected gain setting and the monitored temperature differential from said temperature monitoring system.

2. The differential calorimeter of claim 1 wherein the output signal is a function of the product of the user-selected gain setting and the monitored temperature differential from said temperature monitoring system.

3. The differential calorimeter of claim 1 further comprising a third heating device coupled to both the reference cell and the sample cell, wherein the temperature monitoring system monitors a temperature of at least one of the reference and sample cells, wherein the control system during operation also causes the third heating device to heat both the sample and reference cells at a user-selected scan rate, said control system having a second output line connected to the third heating device and having a second input line, wherein the temperature monitoring system supplies a signal to the second input line which is a function of the monitored temperature of the at least one of the reference and sample cells, and wherein the control system is configured to generate on its second output line an output signal which is a function of both a user-selected scan rate and the signal on the second input line.

4. The differential calorimeter of claim 3, wherein the control system includes a memory storing a mapping function which maps both the signal on the second input line and the user-selected scan rate to a control parameter and wherein the control system generates an output signal on the second output line that is derived from the control parameter.

5. The differential calorimeter of claim 3, further comprising a power source connected to said third heating device and controlled by the control system.

6. The differential calorimeter of claim 5, wherein said third heating device comprises a first element associated with the sample cell and a second element associated with the reference cell, wherein said first and second elements are connected in series across an output of said power source.

* * * * *